US00PP34997P2

(12) United States Plant Patent
Bernuetz et al.

(10) Patent No.: US PP34,997 P2
(45) Date of Patent: Feb. 21, 2023

(54) ***XEROCHRYSUM* PLANT NAMED 'BONXE 1669'**

(50) Latin Name: *Xerochrysum bracteatum*
Varietal Denomination: Bonxe 1669

(71) Applicants: Andrew Bernuetz, Mulgoa (AU); Shaun L. Rebello, Blair Athol (AU)

(72) Inventors: Andrew Bernuetz, Mulgoa (AU); Shaun L. Rebello, Blair Athol (AU)

(73) Assignee: BONZA BOTANICALS PTY., LTD., Yellow Rock (AU)

( * ) Notice: Subject to any disclaimer, the term of this patent is extended or adjusted under 35 U.S.C. 154(b) by 32 days.

(21) Appl. No.: 17/835,889

(22) Filed: Jun. 8, 2022

(51) Int. Cl.
*A01H 5/02* (2018.01)
*A01H 6/14* (2018.01)

(52) U.S. Cl.
USPC ..... Plt./359
CPC ..... *A01H 6/14* (2018.05)

(58) Field of Classification Search
USPC ..... Plt./359
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Xerochrysum* plant named 'Bonxe 1669', characterized by its upright, mounding and uniform plant habit; vigorous growth habit; freely flowering habit; relatively large inflorescences with purplish red and pale purple bi-colored involucral bracts; and strong peduncles that hold the inflorescences above the foliar plane.

1 Drawing Sheet

Figure 1:
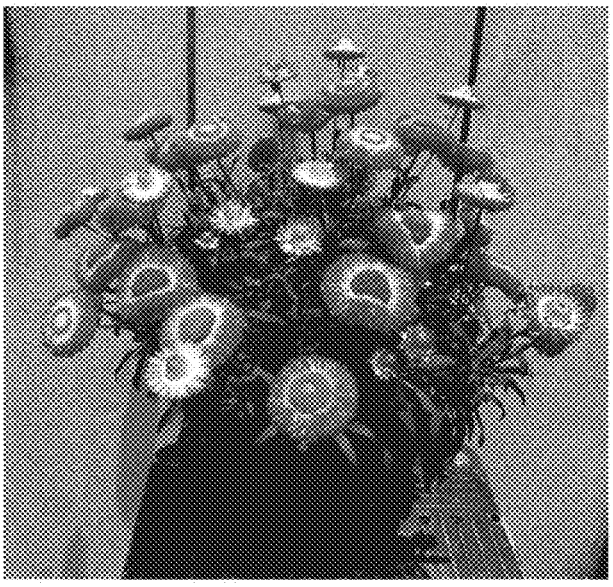

Botanical designation: *Xerochrysum bracteatum.*
Cultivar denomination: 'BONXE 1669'.

BACKGROUND OF THE INVENTION

The present invention relates to a new and distinct cultivar of *Xerochrysum* plant, botanically known as *Xerochrysum bracteatum*, and hereinafter referred to by the name 'Bonxe 1669'.

The new *Xerochrysum* plant is a product of a planned breeding program conducted by the Inventors in Yellow Rock, New South Wales, Australia. The objective of the breeding program is to create and develop new upright *Xerochrysum* cultivars with upright and uniformly mounded plant habit, freely flowering habit and attractive inflorescences and inflorescence buds.

The new *Xerochrysum* plant originated from a cross-pollination by the Inventors on Sep. 2, 2015 of a proprietary selection of *Xerochrysum bracteatum* identified as code number 14-6, not patented, as the female, or seed, parent with a proprietary selection of *Xerochrysum bracteatum* identified as code number 14-60, not patented, as the male, or pollen, parent. The new *Xerochrysum* plant was discovered and selected by the Inventors as a single flowering plant within the progeny of the stated cross-pollination in a controlled greenhouse environment in Yellow Rock, New South Wales, Australia on Aug. 1, 2016.

Asexual reproduction of the new *Xerochrysum* plant by terminal cuttings in a controlled greenhouse environment in Yellow Rock, New South Wales, Australia since August, 2016, has shown that the unique features of this new *Xerochrysum* plant are stable and reproduced true to type in successive generations.

SUMMARY OF THE INVENTION

Plants of the new *Xerochrysum* have not been observed under all possible combinations of environmental and cultural conditions. The phenotype may vary somewhat with variations in environment such as temperature and light intensity, without, however, any variance in genotype.

The following traits have been repeatedly observed and are determined to be the unique characteristics of 'Bonxe 1669'. These characteristics in combination distinguish 'Bonxe 1669' as a new and distinct *Xerochrysum* plant:

1. Upright, mounding and uniform plant habit.
2. Vigorous growth habit.
3. Freely flowering habit.
4. Relatively large inflorescences with purplish red and pale purple bi-colored involucral bracts.
5. Strong peduncles that hold the inflorescences above the foliar plane.

In side-by-side comparisons, plants of the new *Xerochrysum* differ primarily from plants of the female parent selection in the involucral bract color as involucral bracts of plants of the new *Xerochrysum* are purplish red and pale purple bi-colored whereas involucral bracts of plants of the female parent selection are creamy white in color.

In side-by-side comparisons, plants of the new *Xerochrysum* differ primarily from plants of the male parent selection in the involucral bract color as involucral bracts of plants of the new *Xerochrysum* are purplish red and pale purple bi-colored whereas involucral bracts of plants of the male parent selection are pink in color.

Plants of the new *Xerochrysum* can be compared to plants of the *Bracteantha bracteata* 'Bonxero 148', disclosed in U.S. Plant Pat. No. 30,398. In side-by-side comparisons, plants of the new *Xerochrysum* differ primarily from plants of 'Bonxero 148' in the following characteristics:

1. Plants of the new *Xerochrysum* are broader than plants of 'Bonxero 148'.
2. Plants of the new *Xerochrysum* are more freely branching than plants of 'Bonxero 148'.

3. Plants of the new *Xerochrysum* have smaller leaves than plants of 'Bonxero 148'.
4. Plants of the new *Xerochrysum* are more freely flowering than plants of 'Bonxero 148'.
5. Involucral bracts of plants of the new *Xerochrysum* are purplish red and pale purple bi-colored whereas involucral bracts of plants of 'Bonxero 148' are bright yellow in color.
6. Plants of the new *Xerochrysum* have shorter peduncles than plants of 'Bonxero 148'.

BRIEF DESCRIPTION OF THE PHOTOGRAPHS

The accompanying photographs illustrate the overall appearance of the new *Xerochrysum* plant. These photographs show the colors as true as it is reasonably possible to obtain in colored reproductions of this type. Colors in the photographs may differ slightly from the color values cited in the detailed botanical description which accurately describe the colors of the new *Xerochrysum* plant.

The photograph at the top of the sheet (FIG. 1) is a side perspective view of a typical flowering plant of 'Bonxe 1669' grown in a container.

Figure 2:
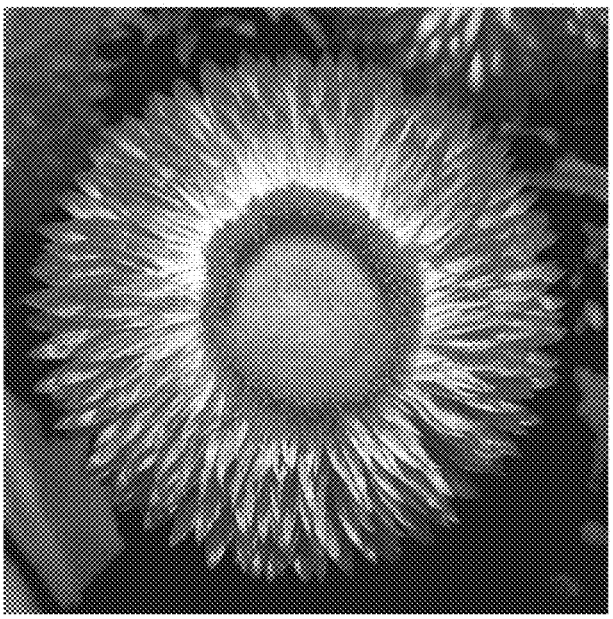

The photograph at the bottom of the sheet (FIG. 2) is a close-up view of a typical inflorescence of 'Bonxe 1669'.

DETAILED BOTANICAL DESCRIPTION

The aforementioned photographs and following observations and measurements describe plants grown during the early summer in 24-cm container in an outdoor nursery in Higashiomi, Shiga, Japan and under conditions and practices which approximate those generally used in commercial *Xerochrysum* production. During the production of the plants, day temperatures averaged 23° C. and night averaged 13° C. Measurements and numerical values represent averages for typical flowering plants. Plants were four months old when the photographs were taken and five months old when the detailed description was taken. In the following description, color references are made to The Royal Horticultural Society Colour Chart, 2001 Edition, except where general terms of ordinary dictionary significance are used.

Botanical classification: *Xerochrysum bracteatum* 'Bonxe 1669'.

Parentage:

*Female, or seed, parent*.—Proprietary selection of *Xerochrysum bracteatum* identified as code number 14-6, not patented.

*Male, or pollen, parent*.—Proprietary selection of *Xerochrysum bracteatum* identified as code number 14-60, not patented.

Propagation:

*Type*.—Terminal vegetative cuttings.

*Time to initiate roots, summer*.—About seven days at temperatures about 18° C. to 21° C.

*Time to initiate roots, winter*.—About ten days at temperatures about 18° C. to 21° C.

*Time to produce a rooted cutting, summer*.—About three weeks at temperatures about 18° C. to 21° C.

*Time to produce a rooted cutting, winter*.—About four weeks at temperatures about 18° C. to 21° C.

*Root description*.—Fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant form and growth habit*.—Upright, mounding and uniform plant habit with inflorescences held above the foliage on strong peduncles; vigorous growth habit.

*Plant height*.—About 41 cm.

*Plant diameter or spread*.—About 65 cm.

*Lateral branches*.—Quantity per plant: Freely branching habit with about 25 lateral branches per plant. Length: About 20.4 cm. Diameter: About 3.6 mm. Internode length: About 1.5 cm. Aspect: Upright to somewhat outwardly. Strength: Strong. Texture: Rough, moderately pubescent. Color: Close to 143B.

*Leaf description*.—Arrangement: Alternate, simple; sessile. Length: About 7.1 cm. Width: About 1.2 cm. Shape: Linear. Apex: Acuminate. Base: Attenuate. Margin: Entire; not undulate. Texture, upper and lower surfaces: Rough, glabrous. Venation pattern: Pinnate; reticulate. Color: Developing leaves, upper surface: Close to 138A. Developing leaves, lower surface: Close to 138B. Fully expanded leaves, upper surface: Close to 137B; venation, close to 146C. Fully expanded leaves, lower surface: Close to 138A; venation, close to 138B.

Inflorescence description:

*Appearance*.—Terminal double-type inflorescence form with narrowly deltoid to lanceolate involucral bracts; involucral bracts and disc florets developing acropetally on a capitulum; inflorescences positioned above the foliar plane on strong peduncles; inflorescences face mostly upright.

*Flowering habit*.—Freely flowering habit; about 52 inflorescences develop per plant during the flowering season.

*Fragrance*.—None detected.

*Time to flower*.—In Japan, plants begin to flower about 21 weeks after planting and in the garden, plants flower continuously from the spring through the autumn.

*Post-production longevity*.—Inflorescences maintain good substance for about seven to ten days on the plant; inflorescences persistent.

*Inflorescence buds*.—Height: About 1.4 cm. Diameter: About 1.2 cm. Shape: Ovoid with acute apex. Color: Distally, close to 64B and proximally, close to 186D.

*Inflorescence size*.—Diameter: About 5.8 cm. Depth (height): About 1.3 cm. Disc diameter: About 2.2 cm. Disc height: About 7.4 mm.

*Receptacles*.—Diameter: About 2.5 cm. Height: About 6.1 mm. Color: Close to 150D.

*Involucral bracts*.—Quantity per inflorescence and arrangement: About 275 arranged in numerous whorls; bracts imbricate. Length: About 1.8 cm. Width: About 5 mm. Shape: Narrowly deltoid to lanceolate. Apex: Acuminate. Base: Truncate. Margin: Entire. Texture, upper and lower surfaces: Smooth, glabrous; papery. Orientation: Initially upright becoming horizontal with development. Color: When opening and fully opened, upper surface: Close to 64B; towards the base, close to 69D. When opening and fully opened, lower surface: Close to 70B; towards the base, close to N155D.

*Disc florets*.—Quantity per inflorescence and arrangement: Numerous disc florets are spirally arranged in the center of the receptacle. Length: About 1.2 cm. Diameter, distally: About 0.7 mm. Diameter, proximally: About 0.3 mm. Shape: Tubular; apex dentate, five-pointed. Texture, inner and outer surfaces: Smooth, glabrous. Color: When developing, inner and outer surfaces: Close to 25A. Fully developed, inner and outer surfaces: Towards the apex, close to 25A; mid-section, close to 13C; towards the base, close to 149D.

*Peduncles*.—Length: About 6.5 cm. Diameter: About 2.7 mm. Strength: Strong. Aspect: Upright to somewhat outwardly. Texture: Rough, pubescent. Color: Close to 138A.

*Reproductive organs*.—Androecium: Quantity per disc floret: About five. Filament length: About 4.2 mm. Filament color: Close to 157D. Anther size: About 1.5 mm by 0.7 mm. Anther shape: Lanceolate. Anther color: Close to 23A. Pollen amount: None observed. Gynoecium: Quantity per disc floret: One. Pistil length: About 9.2 mm. Stigma shape: Biparted. Stigma color: Close to 23A. Style color: Close to 157D. Ovary color: Close to 155A.

*Seeds and fruits*.—To date, seed and fruit production has not been observed on plants of the new *Xerochrysum*.

Pathogen & pest resistance: To date, plants of the new *Xerochrysum* have not been shown to be resistant to pathogens and pests common to *Xerochrysum* plants.

Temperature tolerance: Plants of the new *Xerochrysum* have been observed to tolerate temperatures ranging from about 0° C. to about 35° C.

It is claimed:

1. A new and distinct *Xerochrysum* plant named 'Bonxe 1669' as illustrated and described.

* * * * *